United States Patent [19]

Meric et al.

[11] 4,024,407
[45] May 17, 1977

[54] DEVICE FOR MEASURING THE DUST CONTENT OF A GAS STREAM

[75] Inventors: Jean-Paul Meric; Raymond Peltier, both of Paris, France

[73] Assignee: Centre d'Etudes et de Recherches de l'Industrie des Liants Hydrauliques, Paris, France

[22] Filed: May 15, 1975

[21] Appl. No.: 577,798

[30] Foreign Application Priority Data

May 20, 1974 France .............................. 74.17446

[52] U.S. Cl. .................................. 250/574; 356/207
[51] Int. Cl.² ....................................... G01N 21/26
[58] Field of Search .......... 250/573, 574, 575, 576; 340/237 S; 356/207

[56] References Cited

UNITED STATES PATENTS

| | | | |
|---|---|---|---|
| 2,966,092 | 12/1960 | Hartridge | 356/207 |
| 3,317,730 | 5/1967 | Hilsum | 356/207 |
| 3,809,913 | 5/1974 | Prellwitz | 250/575 |
| 3,954,342 | 5/1976 | Boeke | 340/237 S |

Primary Examiner—David C. Nelms
Attorney, Agent, or Firm—Browdy and Neimark

[57] ABSTRACT

A device for measuring dust content in a gas stream comprising a light source, a photosensitive receiver, and means to direct an essentially dust free stream against the main gas stream to form a dust curtain into which the beam penetrates and reflects to the receiver.

8 Claims, 7 Drawing Figures

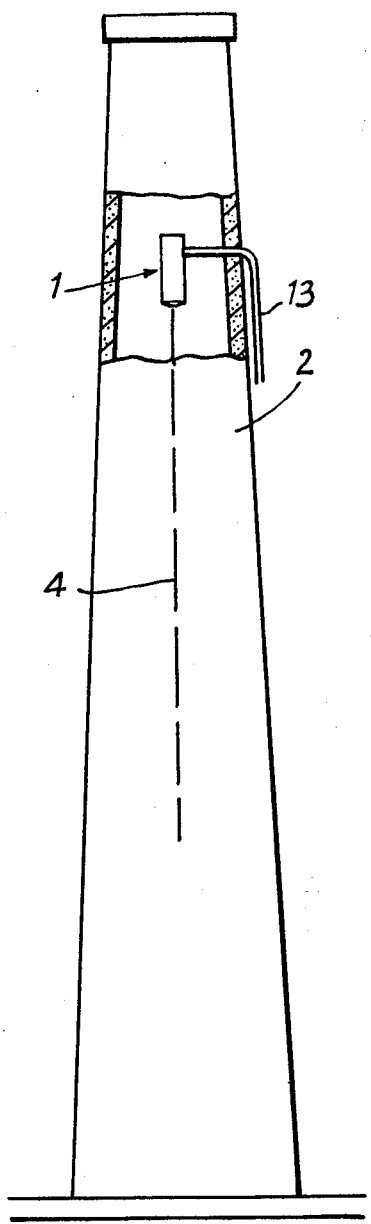
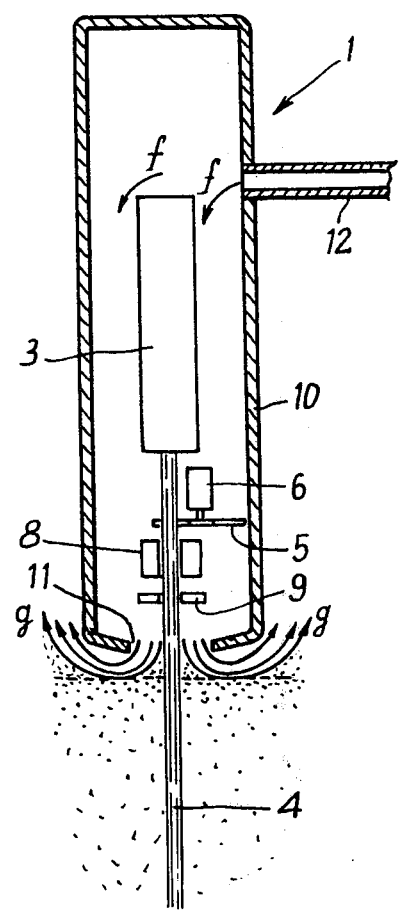
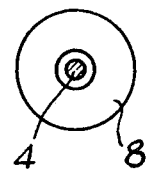
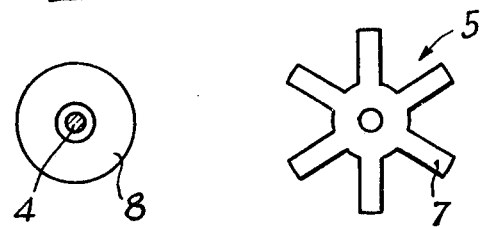

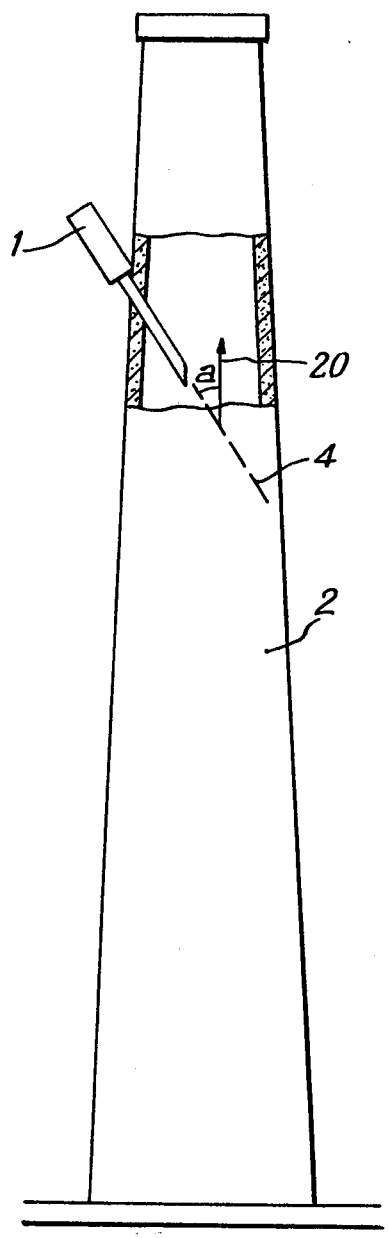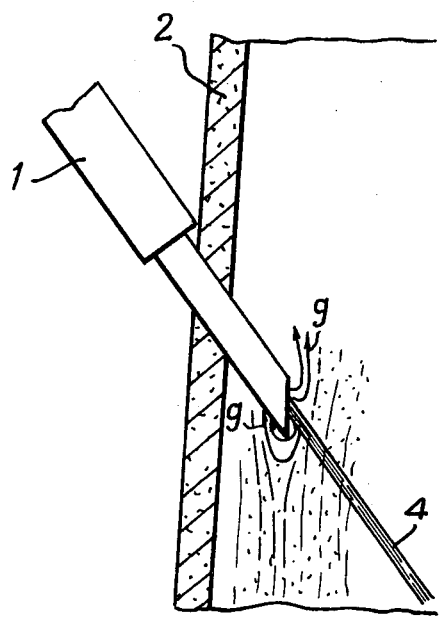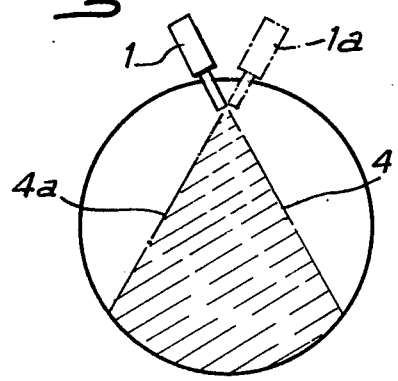

DEVICE FOR MEASURING THE DUST CONTENT OF A GAS STREAM

FIELD OF THE INVENTION

The present invention relates to a device for measuring the dust content of a gas stream and, more particularly, to such a device for use in an air stream in a chimney stack.

BACKGROUND

Devices are already known for measuring the dust content of a gas stream, which include a source emitting electromagnetic radiation, for example light, and a photosensitive receiver. In these known devices the radiation is emitted in a beam directed transversely with respect to the direction of the mean velocity of the gas stream.

In a first embodiment of these known devices, termed "absorption opacity measurement," the receiver is arranged opposite the source with respect to the gas stream. This system has the disadvantage, inter alia, that the measuring signal is weak in the dust content range which is most interesting.

In another type of device of this kind, the receiver is on the same side as the source with respect to the gas stream but at a certain distance from the source, and this type provides measurement of flux scattered sideways by the dust. It is found in this type of device that the measurement signal increases with dust content until it reaches a maximum value, i.e. the saturation value for a certain dust content value. If the dust content increases beyond this value the measurement signal no longer increases but rather decreases, becoming weaker when the dust content is very high.

These two types of known devices also have in common the disadvantage of being applicable only to a small gas stream volume, whatever its dust content.

SUMMARY

An object of the present invention is to remedy these disadvantages and in particular to deliver a measuring signal which increases virtually constantly with the dust content.

According to the invention, a device is provided for measuring the dust content of a gas stream, particularly in a chimney stack, which includes a source disposed to emit a beam of electromagnetic radiation and a photosensitive receiver disposed on the same side as the source with respect to the gas stream and characterized by the receiver being placed in the vicinity of the source and arranged to measure the radiation backscattered by the dust. When the dust content of the gas stream is very low, the volume of measurement is very large. When the dust content in the gas stream is very high this volume decreases, but the measuring signal continues to increase because of the increase in the density of the scattering particles.

According to an advantageous embodiment of the invention, the device includes means for directing a clean fresh air stream containing practically no dust, in front of the beam source and the receiver. It thus forms, in front of the device, a kind of dust certain which the beam penetrates to a greater or lesser depth according to the amount of dust in the gas. Moreover, this clean fresh air cools the device.

According to a preferred embodiment, the beam of radiation is modulated and the receiver includes a synchronous detector. The device can also include an interference filter in front of the source and the receiver to eliminate spurious effects due to heat radiation and natural light. The radiation source is preferably a laser and the receiver is preferably disposed coaxially with the source.

Other characteristics and advantages of the invention will emerge from the detailed description of embodiments hereinbelow.

BRIEF DESCRIPTION OF DRAWING

In the attached drawing, given as non-limitative examples, several embodiments of the invention are shown.

FIG. 1 is an elevation view, partly in section, showing a chimney stack equipped with a device according to a first embodiment of the invention.

FIG. 2 is a cross section of the device shown in FIG. 1.

FIG. 3 is a plan view of the receiver of the device of FIG. 2.

FIG. 4 is a plan view of the modulator of the device of FIG. 2.

FIG. 5 is an elevation view, partly in section, showing a stack equipped with a second embodiment of the invention.

FIG. 6 is a cross section view of the device shown in FIG. 5.

FIG. 7 is a plan view showing the device moving to sweep a gas stream.

DETAILED DESCRIPTION OF EMBODIMENTS

FIG. 1 shows a first embodiment of a device 1 for measuring the dust content of gas circulating in a chimney stack 2 such as a cement works chimney. The device 1 includes an electromagnetic radiation source which, in the embodiment described, is a laser 3 disposed to emit a beam of monochromatic light 4 substantially in the direction of the chimney axis, i.e. parallel to the mean flow velocity of the gases in chimney 2 and toward the bottom of the chimney. A modulator 5 is disposed in the path of beam 4. This modulator may, for example, be a toothed disc, noting FIG. 4, rotating when driven by a motor 6, such that its teeth 7 periodically interrupt the beam 4.

Below the modulator 5, in the path of the beam 4, is disposed a photosensitive receiver 8 comprising for example, a photoelectric cell or an annular-shape photomultiplier, noting FIG. 3, disposed coaxially to laser 3 such as to allow the beam 4 to pass. The receiver can also be disposed outside the path of beam 4 but in its vicinity and in this case obviously does not need to be annular. The output of the receiver 8 is connected to a detector (not shown) synchronous with modulator 5.

Below the receiver 8 is disposed an interference filter 9, annular in shape if the receiver 8 is itself annular. The entire device is mounted inside a case 10, the lower part of which has an opening 11 to allow the beam 4 to pass therethrough, and a connector 12 designed to be connected to a pipe 13 bringing in fresh and substantially dust-free air.

In operation, fresh air passes through the inside of case 10 from the pipe 13 and connector 12 in the direction of arrows $f$, cooling the device, and exhaust through the opening 11 as shown by the arrows $g$. The fresh air, upon exiting from the opening 11, encounters the stack gases which are circulating in the reverse direction, causing the formation of a dust curtain in front of the device 1. The exiting fresh air ensures that the dust cannot penetrate into the case 10.

If the dust content of the stack gases is low, the beam 4 penetrates a substantial distance, e.g. 20–50 meters, into the gases. The receiver 8 measures the luminous flux backscattered by the dust in the whole of this volume. Interference filter 9 eliminates the effect of radiation whose frequency is different from that of beam 4, in particular heat radiation and natural light penetrating the stack. Elimination of spurious radiation is supplemented by the synchronous detector mounted at the output of receiver 8.

When the stack gas dust content is high, the beam 4 can penetrate only a few centimeters. Here, it no longer makes sense to integrate depth-wise the elementary signals produced by the dust in a large volume. Under these conditions, the beam 4 is practically reflected by the dust curtain and produces a high measuring signal. Thus, the measuring signal increases contantly with the dust content; that is, the curve representing this signal versus dust content is monotonic.

In a preferred embodiment shown in FIGS. 5 to 7, the device 1 is disposed such that light beam 4 is inclined at an angle $a$ with respect to the direction of the mean velocity of flow 20 of the gas stream in chimney stack 2. Moreover, the device is disposed laterally with respect to this gas stream. Angle $a$ is preferably about 30°.

In other respects, the construction of the device 1 is similar to that described hereinabove. The second embodiment has the advantages over the first in that the device is better protected from dust and does not impede gas circulation in the stack.

In addition to the advantages already mentioned, the device has the merit of permitting fine exploration of the cross section of the gas stream to be achieved easily in both embodiments. For this purpose one need only to provide means, known of themselves, for causing the device to pivot around an axis, for example, normal to its own axis, for the beam 4 to sweep most of the gas stream section, as seen in the plan view of FIG. 7 wherein the device passes from position 1 to position 1a and the beam from 4 to 4a.

The invention is not, of course, limited to the embodiments described hereinabove and many variations can be made thereto, execution of which is within the skill of the art, without departing from the domain of the invention.

What is claimed is:

1. In a device for measuring the dust content of a gas stream, which may contain dust and has a given average circulation velocity in a given direction, the device including a source arranged to emit a beam of electromagnetic radiation, and a photosensitive receiver placed near the source, on the same side as the source with respect to the gas stream, to measure radiation from the source backscattered by dust in the gas stream, the improvement comprising means for directing a stream of relatively dust-free gas in front of said source and said receiver in a direction having at least a component opposite to said given direction of said average circulation velocity of said gas stream so as to cause accumulation of dust in form of a curtain in front of the device and an increasing output from said receiver with increasing dust content.

2. A device according to claim 1, wherein the radiation beam makes an angle of about 30° with the direction of the mean velocity of the gas stream.

3. Device according to claim 1, further comprising means for modulating the radiation beam located by the receiver, including a synchronous detector.

4. Device according to claim 1, further comprising an interference filter placed in front of the source and the receiver.

5. Device according to claim 1, wherein the radiation source is a laser.

6. Device according to claim 1, wherein the receiver is annular in shape and is disposed coaxially to the source.

7. Device according to claim 1, further comprising means for causing the beam to pivot such as to sweep a section of the gas stream.

8. A device according to claim 1, wherein said means for directing comprise means for directing a stream of relatively dust-free air in a direction substantially opposite to said given direction.

* * * * *